United States Patent [19]
Bok et al.

[11] Patent Number: 5,597,835
[45] Date of Patent: Jan. 28, 1997

[54] ACYL COA:CHOLESTEROL ACYLTRANSFERASE INHIBITORS

[75] Inventors: Song H. Bok; Tae S. Jeong; Sung U. Kim; Byoung M. Kwon; Young K. Kim; Kwang H. Son; Hang W. Lee; Yong K. Kwon, all of Daejeon, Rep. of Korea

[73] Assignee: Korea Institute of Science and Technology, Seoul, Rep. of Korea

[21] Appl. No.: 320,708

[22] Filed: Oct. 7, 1994

[30] Foreign Application Priority Data

Oct. 8, 1993 [KR] Rep. of Korea ................. 1993-20886

[51] Int. Cl.$^6$ ........................ A61K 31/44; C07D 405/00
[52] U.S. Cl. ........................ 514/338; 546/283.1
[58] Field of Search ............................ 546/270; 514/338

[56] References Cited

PUBLICATIONS

CA 121:103731 Jeong et al. 1994.
S. Omura et al., *J. Antibiotics*, 46, 1168–1169 (1993).
K. Kuroda et al., *J. Antibiotics*, 46, 1196–1202 (1993).
H. Tomoda et al., *J. Antibiotics*, 45, 1202–1206 (1992).
H. Tomoda et al., *J. Antibiotics*, 45, 1207–1214 (1992).
S. Naganuma et al., *J. Antibiotics*, 45, 1216–1221 (1992).
H. Tomoda et al., *J. Antibiotics*, 44, 136–143 (1991).

*Primary Examiner*—Jane Fan
*Attorney, Agent, or Firm*—Anderson, Kill & Olick P.C.

[57] ABSTRACT

A novel ACAT inhibitor of formula (I) useful for the treatment of hyperlipidemia produced from *Aspergillus fumigatus* FM-F-37; derivatives of said ACAT inhibitor, which are separated from the culture of *A. fumigatus* FM-F-37 or prepared by a chemical process, also possess ACAT inhibition property.

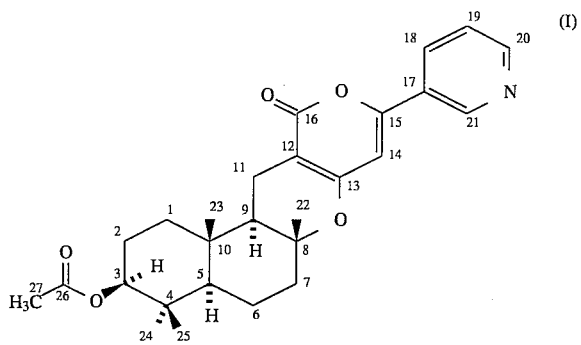

3 Claims, 2 Drawing Sheets

ACYL COA:CHOLESTEROL ACYLTRANSFERASE INHIBITORS

FIELD OF THE INVENTION

The present invention relates to novel acyl CoA: cholesterol acyltransferase ("ACAT") inhibitors, processes for the preparation thereof and pharmaceutical compositions comprising same. More particularly, it pertains to a novel ACAT inhibitor useful for the treatment of hyperlipidemia, said inhibitor being produced by using *Aspergillus fumigatus* FM-F-37; derivatives of said ACAT inhibitor; processes for the preparation of said ACAT inhibitor and derivatives; and pharmaceutical compositions comprising same.

BACKGROUND OF THE INVENTION

In recent years, cancers and cardio-circulatory diseases, e.g, hypertension, arteriosclerosis, hyperlipidemia and hypercholesteremia are increasingly becoming the major causes of death. Therefore, greater efforts and investments are being spent for the development of various medicines to treat these diseases. For example, Merck & Co., Inc. of the U.S. has developed a medicine for lowering blood cholesterol content comprising inhibitors of 3-hydroxy-3-methyl-glutaryl-CoA reductase, which is thought to be necessary for the biosynthesis of cholesterol.

Further, Robin Schnitzer-Polokoff et al. have disclosed that an acyl CoA:cholesterol acyltransferase promotes the esterification of cholesterol in blood, suggesting that the cholesterol content in animal blood can be reduced by inhibiting the ACAT activity (*Comp. Biochem. Physiol*, 99A, 665–670 (1991)).

Thereafter, several ACAT inhibitors isolated from the cultures of various microorganisms have been reported as shown in Table 1 below.

TABLE 1

| ACAT Inhibitors | | |
|---|---|---|
| ACAT inhibitor | Microorganism | Reference |
| Pyripyropenes | *Aspercillus fumigatus* | S. Omura et al., J. Antibiotics, 46, 1168-1169 (1993) |
| AS-183 | *Scedosporium* sp. | K. Kuroda et al., J. Antibiotics, 46, 1196-1202 (1993) |
| Glisoprenins | *Gliocladium* sp. | H. Tomoda et al., J. Antibiotics, 45, 1202-1206 (1992) |
| Enniatins | *Fusarium* sp. | H. Tomoda et al., J. Antibiotics, 45, 1207-1214 (1992) |
| Acaterin | *Pseudomonas* sp. | S. Naganuma et al., J. Antibiotics, 45, 1216-1221 (1992) |
| Purpactins | *Penicillium purpurogenum* | H. Tomoda et al., J. Antibiotics, 44, 136-143 (1991) |

The present inventors have endeavored to discover a novel and potent ACAT inhibitor from a culture of microorganism and, as a result, have succeeded in isolating a novel ACAT inhibitor, GERI-BP001, and its derivatives from the culture of *Aspergillus fumigatus* FM-F-37 which have excellent inhibitory activity against ACAT.

SUMMARY OF THE INVENTION

Accordingly, it is an object of the present invention to provide a novel ACAT inhibitor and its derivatives capable of effectively controlling the cholesterol esterification process.

It is another object of the present invention to provide processes for the preparation of said ACAT inhibitor and its derivatives.

It is a further object of the present invention to provide pharmaceutical compositions comprising said ACAT inhibitor and its derivatives as active ingredients, which are useful for the treatment of cardio-circulatory diseases, especially, hyperlipidemia.

BRIEF DESCRIPTION OF THE DRAWINGS

The above and other objects and features of the present invention will become apparent from the following description of the invention taken in conjunction with the accompanying drawings, in which.

DETAILED DESCRIPTION OF THE INVENTION

Figure 1:
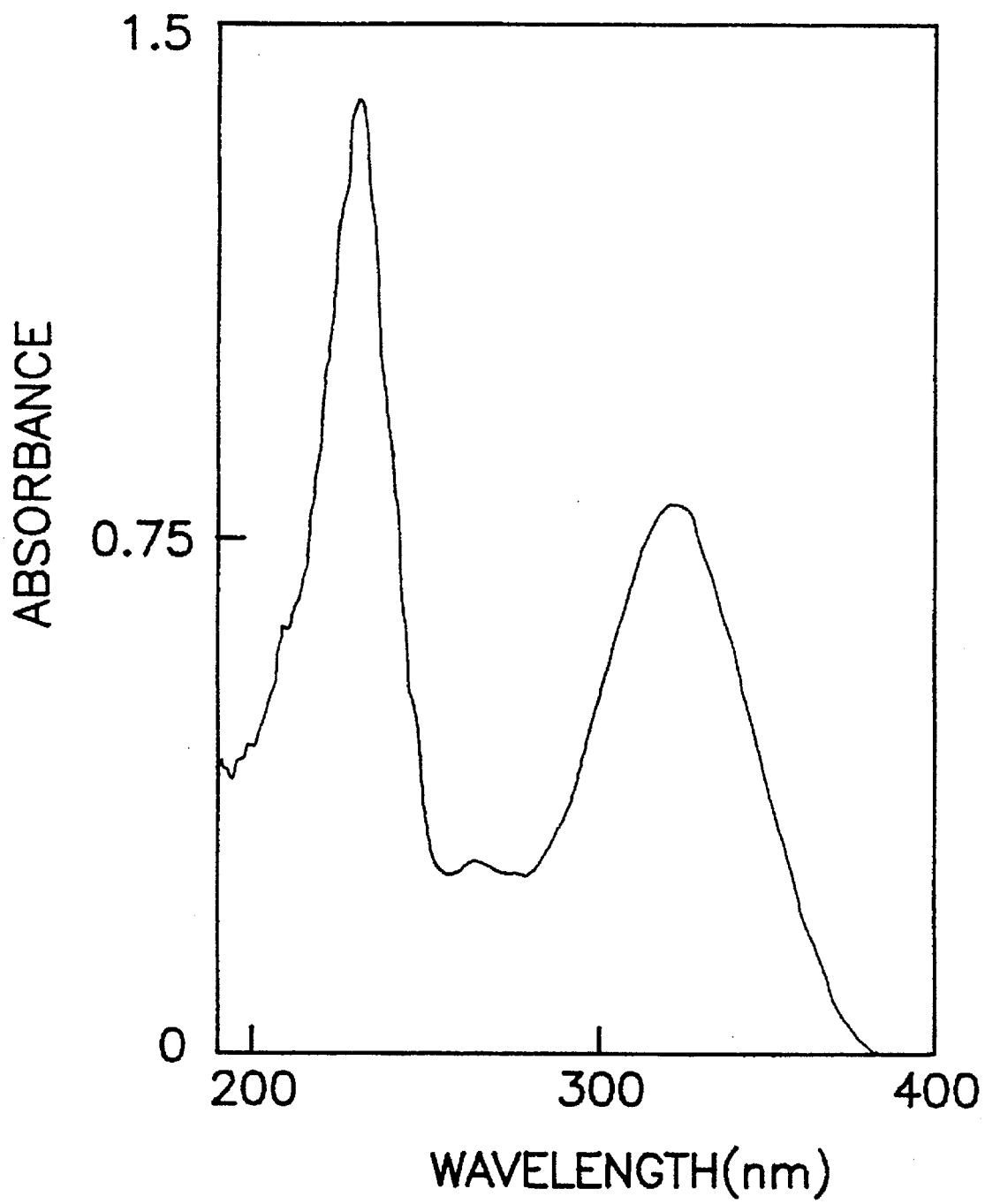
FIG. 1 shows the UV/Visible light spectrum of GERI-BP001.

All references cited herein are hereby incorporated in their entirety by reference.

In accordance with the present invention, there are provided a compound of formula (I) which inhibit ACAT activity and a process for the preparation thereof:

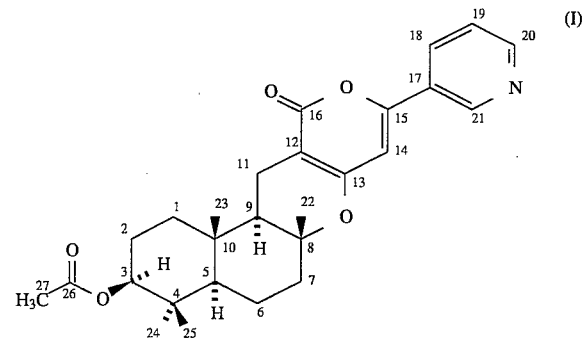

The above compound is designated as GERI-BP001 and may be prepared by culturing *Aspergillus fumigatus* FM-F-37(KCTC 0087BP) and isolating the same from the culture, or may be chemically synthesized by a conventional method.

The physicochemical properties of GERI-BP001 are listed in Table 2.

TABLE 2

| The Physicochemical Properties of GERI-BP001 | |
|---|---|
| Physicochemical Properties | GERI-BP001 |
| Appearance | white powder |
| Polarizing degree ($[\alpha]_D^{18}$ $C_{0.5}$ in $CHCl_3$) | +146.2° |
| Molecular formula | $C_{27}H_{33}NO_5$ |
| Molecular weight (HREI-MS (m/z)) | |
| measured: | 451.2347 |
| calculated: | 451.2358 |
| UV absorption (UV $\lambda_{max}^{MeOH}$(nm)) | 232, 322 |
| IR absorption (IR $v_{max}(cm^{-1})$) | 1246, 1716, 2947 |
| Solubility | |
| soluble: | MeOH, $CHCl_3$ |
| insoluble: | n-hexane, $H_2O$ |

TABLE 2-continued

The Physicochemical Properties of GERI-BP001

| Physicochemical Properties | GERI-BP001 |
| --- | --- |
| Coloring reaction | |
| positive: | 50% $H_2SO_4$, anisaldehyde |
| negative: | ninhydrin |
| Rf value | 0.51 |
| (hexane:EtOAc:MeOH = 5:10:1) | |
| Melting Point | 141–142° C. (decomp.) |

Further, the present invention provides the derivatives of GERI-BP001 having the structural formulas of (I-1), (I-2) and (I-3), respectively, which are designated as GERI-BP001-A, GERI-BP001-B and GERI-BP001-C, respectively.

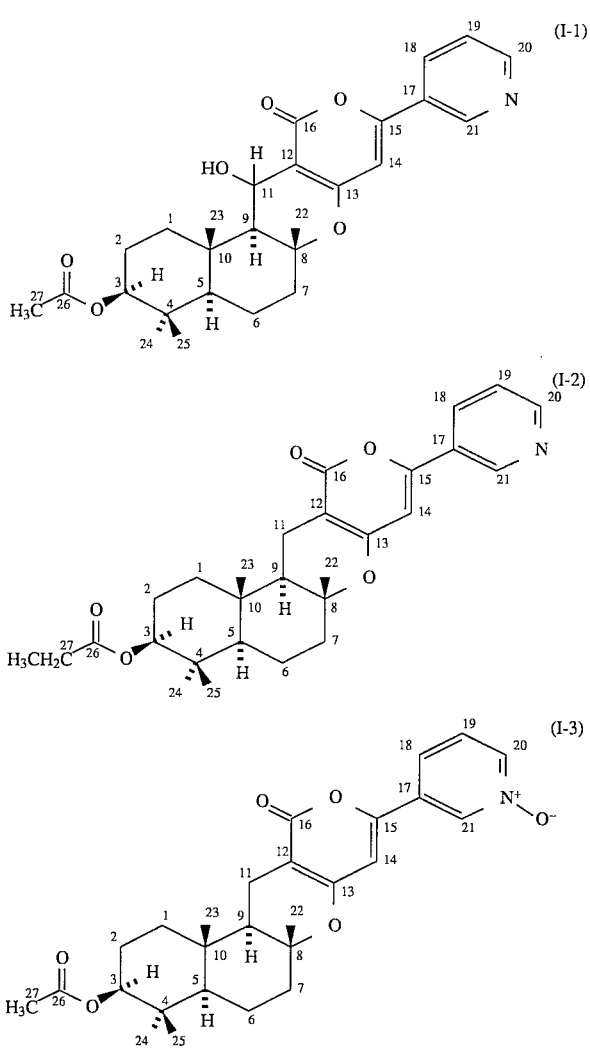

GERI-BP001-A and GERI-BP100-B may be isolated from the culture of the microorganism belonging to the genus Aspergillus, e.g., *Aspergillus fumigatus* FM-F-37; and GERI-BP-001-C can be prepared chemically from GERI-BP001 by a conventional nucleophilic substitution reaction. However, they may also be synthesized chemically by a conventional method.

For the purpose of producing GERI-BP001, GERI-BP001-A and/or GERI-BP001-B by culturing *Aspergillus fumigatus* FM-F-37, any conventional medium which is normally used for the culturing of a microorganism belonging to the genus Aspergillus may be employed; and a preferred medium comprises, per 1 of the medium, 10 to 50 g of soluble starch, 1 to 5 g of pharmamedia, 1 to 5 g of bacto-soytone, 1 to 5 g of polypeptone, 1 to 3 g of $K_2HPO_4$, 1 to 5 g of $CaCO_3$, 0.5 to 1 g of $MgSO_4.7H_2O$, to 2 g of NaCl, 1 to 5 g of yeast extract, 10 to 20 mg of $FeSO_4.7H_2O$, 10 to 50 mg of $MnCl_2.4H_2O$, 10 to 50 mg of $ZnSO_4.7H_2O$ and 1 to 20 mg of $CoCl_2.6H_2O$ and has a pH ranging from 6 to 8.

More preferably, the medium comprises, per 1l of the medium, 2 g of soluble starch, 4 g of pharmamedia, 3 g of bacto-soytone, 2 g of polypeptone, 1 g of $K_2HPO_4$, 3 g of $CaCO_3$, 0.5 g of $MgSO_4.7H_2O$, 2 g of NaCl, 1 g of yeast extract, 20 mg of $FeSO_4.7H_2O$, 10 mg of $MnCl_2.4H_2O$, 10mg of $ZnSO_4.7H_2O$ and 5 mg of $CoCl_2.6H_2O$ and has a pH of 7.0.

In addition, in the early stage of the culture, the culturing of the microorganism is preferably carried out in an aerobic condition at a temperature ranging from 25° to 37° C. while adjusting the pH of the culture medium to a range from 5 to 8 and maintaining the aeration rate ranging from 10 to 20 l/min., the agitation speed ranging from 100 to 200 rpm and the concentration of dissolved oxygen at more than 20%. After 21 hours, the culturing may be continued at a temperature ranging from 25° to 37° C. while adjusting the pH of the culture medium to a range from 5 to 8 and maintaining the aeration rate ranging from 20 to 80 l/min., the agitation speed ranging from 100 to 200 rpm and the concentration of dissolved oxygen at more than 20%.

Upon the completion of the culturing of said microorganism, the culture medium may be filtered through a cotton wool to collect cells, which may then be extracted with acetone and ethyl acetate to obtain a crude extract, which may be further purified by using silica gel column chromatography and high performance liquid chromatography (HPLC). As a result, GERI-BP001, GERI-BP001-A and GERI-BP001-B can be obtained respectively by employing their different retention times during the HPLC.

Further, GERI-BP001-C may be prepared from GERI-BP001 by a conventional nucleophilic substitution wherein GERI-BP001 is reacted with active oxygen under an anhydrous condition.

On the other hand, the ACAT inhibiting activities of GERI-BP001 and its derivatives can be determined in accordance with a modified method of Tabas et al. described in *J. Biol. Chem.*, 261, 3147–3154 (1986). The inhibitor concentration which reduces the activity of ACAT by 50%, i.e., $IC_{50}$, ranges from 70 to 80 μM, from 140 to 150 μM, from 70 to 80 μM and from 110 to 120 μM in case of GERI-BP001, GERI-BP001-A, GERI-BP001-B and GERI-BP001-C, respectively. Further, acute toxic effect was not found in rats administered with GERI-BP001 or any of its derivatives.

GERI-BP001 and its derivatives of the present invention can be used as a treating agent for hyperlipidemia, especially, for lowering blood cholesterol content owing to their activities for blocking the absorption of cholesterol by inhibiting the ACAT which promotes the esterification of cholesterol.

Therefore, the present invention provides pharmaceutical compositions comprising the compound of formula (I) or any of its three derivatives as an active ingredient. More particularly, the present invention provides pharmaceutical compositions useful for treating hyperlipidemia comprising the compound of formula (I) or its derivatives in an effective amount to inhibit acyl CoA:cholesterol acyltransferase in association with a pharmaceutically acceptable carrier.

Further, the compositions of the present invention may be blended with conventional excipients, e.g., fillers, anti-aggregating agents, binders, lubricants, flavors, in accordance with a conventional method.

The following Examples are intended to further illustrate the present invention without limiting its scope.

Percentages given below for solids in solid mixtures, liquids in liquids and solids in liquids are on a wt/wt, vol/vol and wt/vol basis, respectively, unless specifically indicated otherwise.

Example 1

Separation and Identification of a Microorganism which exhibits ACAT inhibiting activities A soil sample collected in Mt. Deogyu located in Jeollabukdo, Korea was diluted with sterilized water and spread on a conventional potato-dextrose agar medium (potato (infusion form) 200 g, dextrose 20 g and agar 20 g per l, pH 5.1; Difco Products, U.S.A.) and then incubated at 37° C. for 5 days to collect fungal colonies.

Said fungal colonies were identified in accordance with a method described by R. A. Samson and J. I. Pitt in *Advances in Penicillium and Aspergillus Systematics* (1985, Plenum Press, New York and London) and in *Modern Concepta in Penicillium and Aspergillus Classification* (1985, Plenum Press, New York and London) as a strain belonging to *Aspergillus fumigatus*, whose morphological characteristics, when they were cultured on Czapek agar medium (0.2% $NaNO_3$, 0.1% $K_2HPO_4$, 0.05% $MgSO_4.7H_2O$, 0.05% KCl, 0.001% $FeSO_4.7H_2O$, 3% sucrose, 1.5% agar) at 25° C. for 1 week, were determined to be as follows:

Colony Size (diameter): 4.5 cm

Conidiophore: dense felt with dark green color

Conidial head: columnar-shaped

Conidiophores: short and smooth walled hypha with slightly green color in upper part vesicles: clavate form Phialids: directly attached to vesicles Conidia: round-walled elliptical form The separated fungus was designated as *Aspergillus fumigatus* FM-F-37 and deposited at Korean Collection for Type Cultures (KCTC) (Address: GERI, KIST, P.O. Box 17, Daeduk Danji, Taejon, 305–606, Republic of Korea) on Sep. 27, 1993 with the accession number of KCTC 0087BP under the terms of the Budapest Treaty on the International Recognition of the Deposit of Microorganisms for the Purpose of Patent Procedure.

Example 2

Culture of *Aspergillus fumigatus* FM-F-37

*Aspergillus fumigatus* FM-F-37 was inoculated into each of two 1000 ml Erlenmeyer flasks each containing 200 ml of sterilized seed culture medium (pH 5.8) comprising 2% glucose, 0.5% yeast extract, 0.5% polypeptone, 0.1% $KH_2PO_4$ and 0.05% $MgSO_4.7H_2O$ and then cultured with shaking at 30° C. for 2 days. 20 to 50 ml of the resulting culture was inoculated into each of four 5000 ml Erlenmeyer flasks containing 1,500 ml of said seed culture medium and then cultured with shaking at 30° C. for 3 days.

Into a 100 l bioreactor was added 70 l of culture medium comprising 2% soluble starch, 0.4% pharmamedia, 0.3% bacto soytone, 0.2% polypeptone, 0.1% $K_2HPO_4$, 0.3% $CaCO_3$, 0.05% $MgSO_4.7H_2O$, 0.2% NaCl, 0.1% yeast extract, 20 mg/l $FeSO_4.7H_2O$, 10 mg/l $MnCl_2.4H_2O$, 10 mg/l $ZnSO_4.7H_2O$ and 5 mg/l $COCl_2.6H_2O$.

The medium was steam-sterilized at 121° C. for 30 minutes and then the whole seed culture obtained above was added thereto and cultured for 21 hours maintaining the pH of 6.0, temperature of 30° C., agitation speed of 100 rpm, aeration rate of 20 l/min. with dissolved oxygen concentration of more than 20%. After 22 hours from the start of the culturing, 5l of sterilized distilled water was added to the culture medium and the culturing was continued, while maintaining the pH of 6.0, temperature of 30° C., agitation speed of 200 rpm and aeration rate of 70 l/min. The culturing was carried out for 141 hours in all and the pH of the culture solution obtained upon the completion of culture was 5.8.

Example 3

Isolation and purification of GERI-BP001, GERI-BP001-A and GERI-BP001-B

GERI-BP001 and its derivatives GERI-BP001-A and GERIBP-001-B were isolated from the culture of *Aspergillus fumigatus* FM-F-37 in accordance with the following procedures.

8 l of culture of *Aspergillus fumigatus* FM-F-37 obtained in Example 2 was passed through cotton wool to separate cells and 2 μl of acetone was added to the separated cells. The resulting suspension was stirred for 12 hours and then filtered through cotton wool to separate cells. The cells were extracted twice with acetone and the cell extract was concentrated under a reduced pressure of 635 mmHg(concentrate 1).

6 to 6.5 l of the supernatant obtained from the culture of *Aspergillus fumigatus* FM-F-37 by centrifugation was adsorbed in an Amberlite XAD-7 adsorption column (10.5× 45 cm, Rohm & Hass Company, U.S.A.) at a flow rate of 40 ml/min., the column was washed with 8 l of distilled water to remove impurities and then methanol was added to the column to elute active materials remaining in column. The eluates were collected by 500ml fractions and.each fraction was screened by using the method described in Example 6 hereof to collect the fractions exhibiting ACAT inhibiting activities. The collected fractions were concentrated under a reduced pressure of 635 mmHg to obtain a yellowish brown concentrate (concentrate 2).

Concentrates 1 and 2 were combined and distilled water was added thereto to a final volume of 500 ml and the resulting solution was extracted three times each with 500 ml of ethyl acetate. The resulting extract was dried under a reduced pressure of 635 mmHg to obtain 7.3 g of yellowish brown oily material.

The oily material thus obtained was adsorbed onto 15 g of silica gel (Merck, U.S.A., product No. 9385) and the silica gel was added onto 150 g of fresh silica gel stuffed in a column (4.5×20 cm) by using hexane-ethyl acetate (1:1). The adsorbed oily material was eluted with hexane-ethyl acetate (1:1) solution wherein the proportion of ethyl acetate was increased gradually to 80%, from the silica gel column. The fractions comprising active materials were collected and then concentrated under a reduced pressure of 635 mmHg.

The resulting concentrate was chromatographed by employing a high performance liquid chromatograph (Perkin-Elmer Cetus, U.S.A.) equipped with an Ultracarb 10 ODS HPLC column (250×21.2 mm, 10 μm, Phenomenex, U.S.A.) with 90% methanol at a flow rate of 5 ml/min. to elute the active material, and then the UV absorption value at 320 nm for each eluted fraction was determined.

Determination of enzyme activity for GERI-BP001-A revealed its absorption peak at the retention time (Rt) of 26 minutes, GERI-BP001 peak at Rt of 34 minutes, and GERI-BP001-B peak at Rt of 43 minutes. Finally, 16 mg of GERI-BP001, 5 mg of GERI-BP001-A and 4 mg of GERI-BP001-B were obtained by using the HPLC.

Example 4

Synthesis of GERI-BP001-C 50 mg of GERI-BP001 was added to 30 ml of chloroform and dissolved by stirring at 25° C. for 3 hours. 60 mg of 3-chloroperoxybenzoic acid dissolved in 50 ml of chloroform was added slowly to the resulting solution and the reaction mixture was stirred at room temperature for 3 hours. The resulting mixture was poured into 100 ml of 10% sodium carbonate solution and extracted with 100 ml of chloroform. The organic layer was washed with water, dried and evaporated to obtain the crude product, which was purified by using silica gel column chromatography with chloroform:methanol (15:1) as an eluent to obtain 30 mg of GERI-BP001-C as white powder.
Yield: 55%
m.p.: 150° C. (decomposed)
IR(film, $cm^{-1}$): 1720.2(C=O), 1697.4(C=O), 1557.3(N—O), 1240(C—O)
Mass(m/e):HREIMS measured 467.2317 calculated 467.2307

Example 5

Structure of ACAT inhibitors

The following instrumental analyses were carried out to determine the structures of GERI-BP001 and its derivatives.
1) UV-Visible light spectroscopy 3.2 mg of purified GERI-BP001 was dissolved in 100 ml of 100% methanol and its absorption wavelength was determined by using a UV-Vis spectrophotometer(model UV-265, Shimadzu, Japan). Two absorption peaks were observed at 232 nm and 322 nm, respectively (see FIG. 1).
2) IR spectroscopy 2 mg of GERI-BP001 was dissolved in 0.1 ml of chloroform and the solution was applied to AgBr window, dried and then analyzed with an IR spectroscope (model FTS-80, Bio-Rad Digilab Division). The analysis showed that GERI-BP001 has an absorption peak for CH group at 2947 $cm^{-1}$, absorption peak for carbonyl group at 1716 $cm^{-1}$ and absorption peak for aromatic group comprising nitrogen atom at 1246 $cm^{-1}$, respectively.

In addition, the IR spectroscopy using GERI-BP001-C further revealed an absorption peak representing the presence of $N^+$—$O^-$ group at 1557.3 $cm^{-1}$.
3) Mass spectrometry The molecular weight of GERI-BP001 was determined with a VG70-VSEQ mass spectrometer (Vacuum Generator, UK) by using High-Resolution Electron Impaction (HREI)-MS method. As a result, [M$^+$] ionic molecular peak was detected at 451.2347. The molecular formula of GERI-BP001 was determined to be $C_{27}H_{33}NO_5$ from the molecular weight of 451.2347. Using the same procedure, the molecular formula of GERI-BP001-A (molecular weight: measured 467.2354, calculated 467.2308) was determined to be $C_{27}H_{33}NO_6$ and that of GERI-BP001-B (molecular weight: measured 465.2492, calculated 465.2515) was determined to be $C_{28}H_{35}NO_5$.
4) NMR spectroscopy GERI-BP001 and its derivatives were dried completely, dissolved in $CDCl_3$ and then put into 5 mm tube, respectively. The NMR spectroscopy was carried out with said tubes by using an NMR spectroscope (AM-300, Bruker, Germany), wherein $^1$H-NMR was detected at 300 MHz and $^{13}$C-NMR was detected at 75 MHz. The $^1$H-NMR data and $^{13}$C-NMR data for GERI-BP001, GERI-BP001-A and GERI-BP001-B are shown in Table 3 and 4.

TABLE 3

$^1$H-NMR (300MHz) data for GERI-BP001, GERI-BP001-A and GERI-BP001-B

| C# | GERI-BP001 | GERI-BP001-A | GERI-BP001-B |
|---|---|---|---|
| 1 | $^\alpha$1.15(1H, dt, 3.4, 12.7) $^\beta$1.77(1H, dt, 3.4, 13.2) | $^\alpha$1.30(1H, dd, 12.0, 7.3) $^\beta$2.12(1H, ddd, 13.4, 5.6, 3.0) | $^\alpha$1.18(1H, dd, 12.1, 4.2) $^\beta$1.79(1H, dt, 13.2, 3.4) |
| 2 | $^{\alpha,\beta}$1.59–1.74 (2H, m) | $^{\alpha,\beta}$1.74–1.79 (2H, m) | $^{\alpha,\beta}$1.60–1.75 (2H, m) |
| 3 | 4.48(1H, dd, 4.7, 11.7) | 4.95(1H, dd, 9.3, 7.1) | 4.50(1H, dd, 11.7, 4.7) |
| 5 | 1.06(1H, dd, 2.0, 12.1) | 1.45(1H, d, 4.1) | 1.08(1H, dd, 12.1, 2.0) |
| 6 | $^\alpha$1.77(1H, dt, 3.4, 13.2) $^\beta$1.42(1H,dd, 2.2, 12.2) | $^\alpha$1.74–1.79 (1H, m) $^\beta$1.59(1H, dd, 9.7, 3.0) | $^\alpha$1.79(1H, dt, 13.2, 3.4) $^\beta$1.43(1H, dd, 12.4, 3.2) |
| 7 | $^\alpha$1.59–1.74 (1H, m) $^\beta$2.11(1H, ddd, 3.1, 3.1, 12.6) | $^\alpha$1.69(1H, dt, 13.4, 4.4) $^\beta$2.12(1H, ddd, 13.4, 5.6, 3.0) | $^\alpha$1.60–1.75 (1H, m) $^\beta$2.12(1H, dt, 12.4, 3.2) |
| 9 | 1.48(1H, dd, 4.8, 12.9) | 1.02(1H, dd, 12.0, 2.2) | 1.50(1H, dd, 12.9, 4.7) |
| 11 | $^\alpha$2.48(1H, dd, 4.7, 17.1) $^\beta$2.21(dd, 12.9, 17.1) | $^\alpha$(OH) 2.82 (br s) $^\beta$(H) 4.95 (d, 4.1) | $^\alpha$2.50(1H, dd, 17.1, 4.7) $^\beta$2.22(1H, dd, 17.1, 12.9) |
| 14 | 6.39(1H, s) | 6.44(1H, s) | 6.40(1H, s) |
| 18 | 8.07(1H, d, 8.1) | 8.08(1H, dt, 8.0, 1.8) | 8.08(1H, dt, 8.0, 2.0) |
| 19 | 7.35(1H, dd, 4.8, 8.0) | 7.35(1H, dd, 8.0, 1.8) | 7.36(1H, dd, 8.0, 4.9) |
| 20 | 8.62(1H, s) | 8.66(1H, s) | 8.63(1H, d, 3.8) |
| 21 | 8.96(1H, s) | 8.99(1H, s) | 8.97(1H, s) |
| 22 | 1.23(3H, s) | 1.63(3H, s) | 1.25(3H, s) |
| 23 | 0.91(3H, s) | 1.35(3H, s) | 0.92(3H, s) |
| 24 | 0.87(3H, s) | 0.87(3H, s) | 0.88(3H, s) |
| 25 | 0.85(3H, s) | 0.89(3H, s) | 0.87(3H, s) |
| 27 | 2.03(3H, s) | 2.04(3H, s) | 2.31(2H, q, 7.6) |
| 28 | | | 1.23(3H,s) |

TABLE 4

$^{13}$C-NMR (75MHz) data for GERI-BP001, GERI-BP001-A and GERI-BP001-B

| C# | GERI-BP001 | GERI-BP001-A | GERI-BP001-B |
|---|---|---|---|
| 1 | 37.09 | 36.78 | 37.13 |
| 2 | 23.41 | 23.33 | 23.48 |
| 3 | 80.07 | 80.29 | 79.81 |
| 4 | 36.70 | 37.75 | 36.76 |
| 5 | 55.00 | 56.06 | 55.04 |
| 6 | 19.21 | 19.53 | 19.25 |
| 7 | 40.16 | 41.36 | 40.20 |
| 8 | 80.79 | 82.24 | 80.84 |
| 9 | 51.36 | 55.63 | 51.40 |
| 10 | 37.69 | 38.05 | 37.80 |
| 11 | 17.25 | 60.44 | 17.30 |
| 12 | 100.22 | 103.33 | 100.28 |
| 13 | 162.76 | 162.75 | 162.79 |
| 14 | 99.34 | 99.57 | 99.37 |
| 15 | 155.58 | 157.13 | 155.63 |
| 16 | 163.95 | 164.22 | 164.00 |
| 17 | 127.58 | 127.35 | 127.62 |
| 18 | 132.71 | 132.94 | 132.76 |

TABLE 4-continued

13C-NMR (75MHz) data for GERI-BP001,
GERI-BP001-A and GERI-BP001-B

| C# | GERI-BP001 | GERI-BP001-A | GERI-BP001-B |
|----|------------|--------------|--------------|
| 19 | 123.56 | 123.64 | 123.58 |
| 20 | 151.01 | 51.42 | 151.06 |
| 21 | 146.59 | 146.80 | 146.64 |
| 22 | 20.64 | 22.14 | 20.69 |
| 23 | 15.10 | 17.02 | 15.14 |
| 24 | 28.02 | 28.26 | 28.07 |
| 25 | 16.55 | 16.55 | 16.63 |
| 26 | 170.81 | 170.92 | 174.16 |
| 27 | 21.19 | 21.25 | 28.00 |
| 28 | | | 9.30 |

Figure 2:
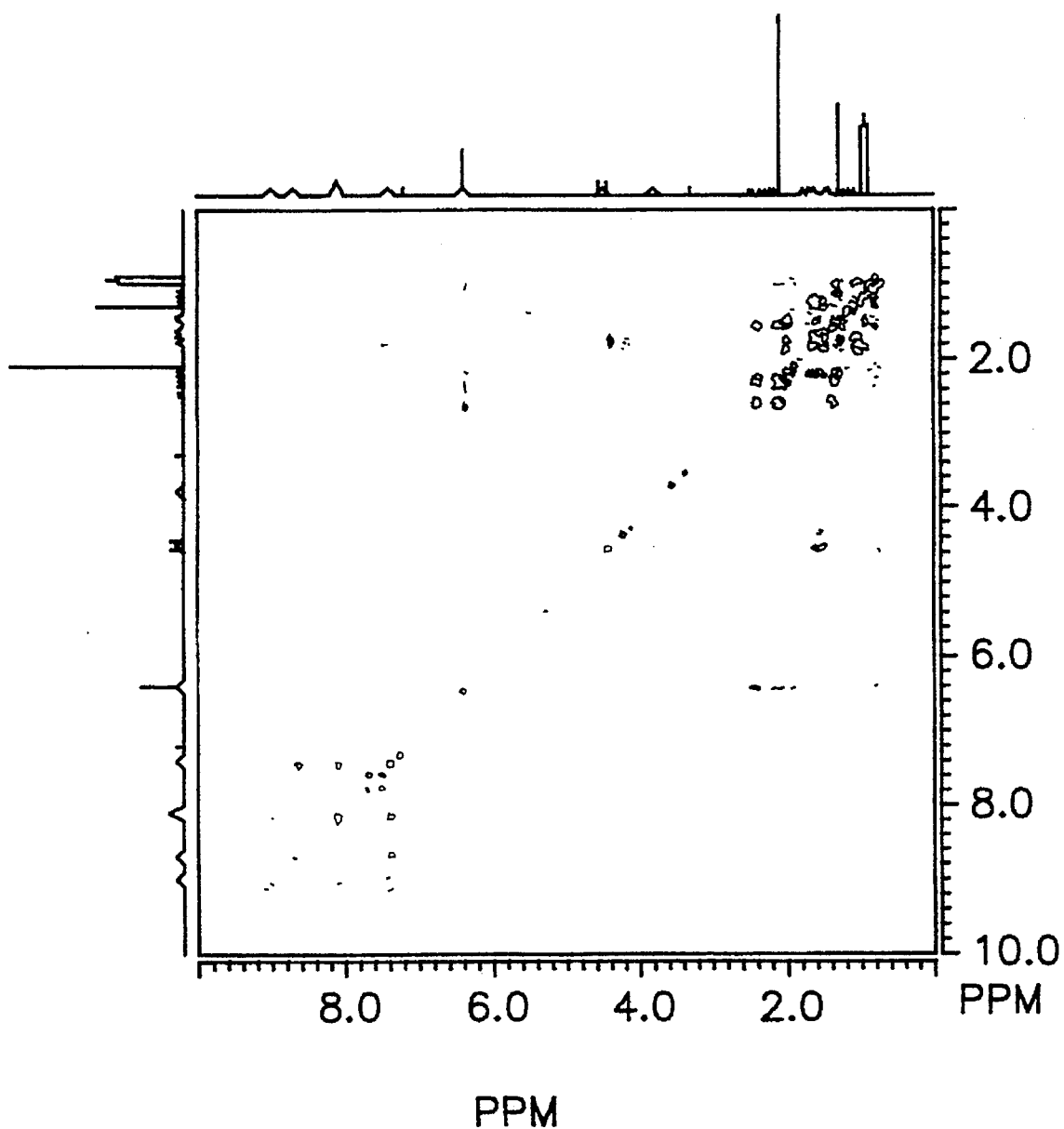
FIG. 2 describes the HOMOCOSY NMR spectrum of GERI-BP001.

As a result of interpretation of $^1$H-NMR spectrum, $^{13}$C-NMR spectrum, 2D-HOMOCOSY (see FIG. 2), 2D-HETEROCOSY, 2D-NOESY and 2D-(H, C)-Long Range COSY spectrum, the molecular structures of GERI-BP001 and its derivatives were determined to consist of 3 parts, i.e., pyridine, α-pyrone and sesquiterpene, and have one ester group.

Therefore, it can be seen from the above analytic results that the structures of the ACAT inhibitors of the present invention are the same as those represented by the above formulas (I), (I-1), (I-2) and (I-3).

Example 6

Assay for ACAT inhibiting activity of GERI-BP001

ACAT activity was determined as follows in accordance with a modified method of Tabas et al. described in *J. Biol. Chem.*, 261, 3147–3154 (1986).

10 μl of sample, 4.0 μl of microsomal enzyme (10 mg/ml of protein) derived from rat liver tissue, 20 μl of analysis buffer(0.5M $KH_2PO_4$, 10 mM dithiothreitol (DTT), pH 7.4), 15 μl of 40 mg/ml bovine serum albumin(essentially free of fatty acids), 2 μl of 20 mg/ml cholesterol and 41 μl of $H_2O$ were mixed together and the resulting mixture was reacted at 37° C. for 15 minutes. 8 μl of [1-$^{14}$C] oleoyl-CoA(0.05 μCi, final concentration of 10 μM) was added to the mixture and the reaction mixture was reacted at 37° C. for 15 minutes.

1 ml of isopropanol-heptane (4:1(v/v)) was added to the mixture to stop the reaction, 0.6 ml of heptane and 0.4 ml of said analysis buffer(5-fold diluted) were added thereto and the resulting mixture was centrifuged at 2,000 g for 2 minutes to obtain the supernatant.

5 ml of scintillation cocktail lipoluma (Lumac Co., U.S.A.) was added to 100 μl of the supernatant obtained above and enzyme activity was determined by detecting the amount of cholesteryl ester in the mixture based on the unit of count per minute (CPM) by using a liquid scintillation counter.

ACAT inhibiting activity was calculated in accordance with the following equation:

Inhibition rate(%) =

$$100 \times \left(1 - \frac{CPM(\text{sample}) - CPM(\text{blank})}{CPM(\text{control}) - CPM(\text{blank})}\right)$$

wherein the blank composition had the same composition as the above sample but without enzyme and GERI-BP001 or its derivatives, and was reacted at 37° C.; and the control had the same composition as the above sample without GERI-BP001 or its derivatives and was reacted at 37° C. for 15 min.

The $IC_{50}$ values of GERI-BP001, GERI-BP001-A, GERI-BP001-B and GERI-BP001-C calculated from their individual inhibiting rate were 70 to 80 μM, 140 to 150 μM, 70 to 80 μM and 110 to 120 μM, respectively.

Example 7

Toxicity of GERI-BP001

5 female ICR mice weighing 23 g were administered via subcutaneous injection with 500 mg/kg of GERI-BP001. Activities of mice were increased and an excited state was induced about 15 minutes after administration. However, those symptoms disappeared about 2 hours after the administration and none of the mice was dead until 4 days after the administration. Therefore, it is judged from the above result that GERI-BP001 does not cause acute toxicity in animals.

While the invention has been described with respect to the above specific embodiments, it should be recognized that various modifications and changes may be made and also fall within the scope of the invention as defined by the claims that follow.

What is claimed is:

1. A compound of formula (I), GERI-BP001:

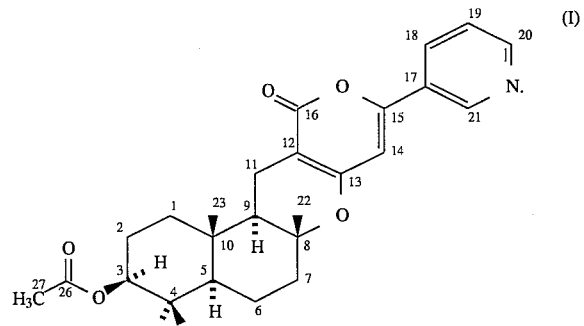

2. A compound of formula (I-1), GERI-BP001-A:

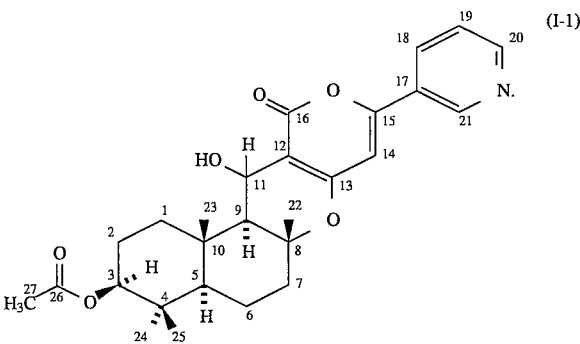

3. A pharmaceutical composition for the treatment of hyperlipidemia, comprising an effective amount of a compound selected from the group consisting of GERI-BP001 and GERI-BP001-A as an active ingredient, and an inert pharmaceutically acceptable carrier.

\* \* \* \* \*